United States Patent [19]

Muraki

[11] Patent Number: 5,696,098
[45] Date of Patent: Dec. 9, 1997

[54] PARTIALLY N-ACYLATED COMPOUND OF CHITOOLIGOSACCHARIDE, SALT THEREOF, AND USE THEREOF

[75] Inventor: Einosuke Muraki, Osaka, Japan

[73] Assignee: Agency of Industrial Science & Technology, Ministry of International Trade & Industry, Tokyo, Japan

[21] Appl. No.: 611,135

[22] Filed: Mar. 5, 1996

[30] Foreign Application Priority Data

Mar. 15, 1995 [JP] Japan .................................. 7-84883

[51] Int. Cl.$^6$ .......................... A61K 31/73; A01N 43/04; C08B 37/08; C07H 5/06
[52] U.S. Cl. ................. 514/55; 536/20; 536/55.2; 536/123.1
[58] Field of Search ..................... 536/20, 123.1, 536/55.2; 514/55

[56] References Cited

U.S. PATENT DOCUMENTS 3,953,608  4/1976  Vanlerberghe et al. ................. 536/20
4,996,307  2/1991  Itoi et al. ................................ 536/20

FOREIGN PATENT DOCUMENTS 28126  6/1981  European Pat. Off. ................ 536/20

Primary Examiner—John Kight
Assistant Examiner—Everett White
Attorney, Agent, or Firm—Oblon, Spivak, McClelland, Maier & Neustadt, P.C.

[57] ABSTRACT

A partially N-acylated compound of chitooligosaccharide consisting essentially of 2 number of acyl glucosamine constituent units, m number of glucosamine constituent units and n number of acetyl glucosamine constituent units, wherein the ratios of l, m and n to the sum of l, m and n are in the respective ranges of 5 to 80%, 20 to 95%, and 0 to 50%, and having an OH radical attached at the 4 position or 1 position of the terminal unit of the composition.

19 Claims, 3 Drawing Sheets

PARTIALLY N-ACYLATED COMPOUND OF CHITOOLIGOSACCHARIDE, SALT THEREOF, AND USE THEREOF

BACKGROUND OF THE INVENTION

1. Field of the Invention

This invention relates to a partially N-acylated compound of chitooligosaccharide, salts thereof, and uses therefor in, i.e., antibacterial agents and cosmetic additives containing the N-acylated compound or salt thereof as active component.

2. Prior Art Statement

Oligosaccharides have been applied in different fields according to the kind of constituent monosaccharide units and have found utility in sweetening agents, moisture retaining agents, diet foods, etc.

As oligosaccharides are highly safe biodegradable substances exhibiting excellent compatibility with human body tissue, they are expected to find utility in the fields of medicine, cosmetics and personal care products.

Heitening concern about cleanliness in recent years has led to the marketing of various products incorporating antibacterial agents, such as clothing, cash cards, and ball point pens. The antibacterial agents incorporated in such products are required not only to be excellent in antibacterial activity but also to be highly safe, because they frequently come in contact with the user's skin.

SUMMARY OF THE INVENTION

In view of the useful qualities of oligosaccharides, the inventor conducted a study for establishing a completely new technique for the utilization of oligosaccharides. He consequently found that partially N-acylated glucosamine oligomer containing N-acetyl glucosamine and an N-acylated compound thereof at a fixed ratio (hereinafter referred to as "chitooligosaccharide") exhibits antibacterial property. The partially N-acylated compound manifests high solubility to water, exhibits little tendency to migrate into living tissue, and is low in toxicity since any of the compound absorbed into a living tissue readily decomposes into glucosamine, a vital constituent. It thus exhibits useful qualities for an antibacterial agent to be incorporated into products which come into contact with the user's skin. Further, since it possesses an ability to retain moisture in addition to the antibacterial property, it proves useful as an additive to cosmetics, personal care articles, ointments, etc.

Specifically, this invention relates to the partially N-acylated compound of a chitooligosaccharide, salts thereof, and antibacterial agents and cosmetic additives making use of the compound or salts thereof.

This invention is directed to a partially N-acylated compound of a chitooligosaccharide essentially consisting of a) l number of acyl glucosamine constituent units represented by the formula;

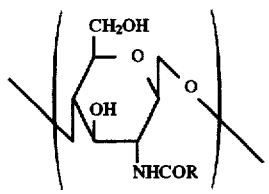

(1)

wherein —COR stands for an acyl radical of 4 to 26 carbon atoms.

b) m number of glucosamine constituent units represented by the formula:

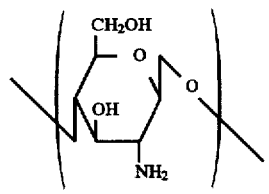

(2)

and c) n number of acetyl glucosamine constituent units represented by the formula:

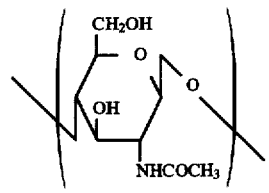

(3)

wherein l, m, and n satisfy the following equations, $l/(l+m+n) \times 100 = 5\text{--}80$, $m/(l+m+n) \times 100 = 20\text{--}95$, $n/(l+m+n) \times 100 = 0\text{--}50$, $l+m+n = 3\text{--}20$, and possessing an OH group at the 4 position or 1 position of the terminal constituent unit and a salt of the compound obtained by the reaction of the amino radical in the glucosamine constituent unit of the compound with an acid.

DESCRIPTION OF THE PREFERRED EMBODIMENTS

Figure 1:
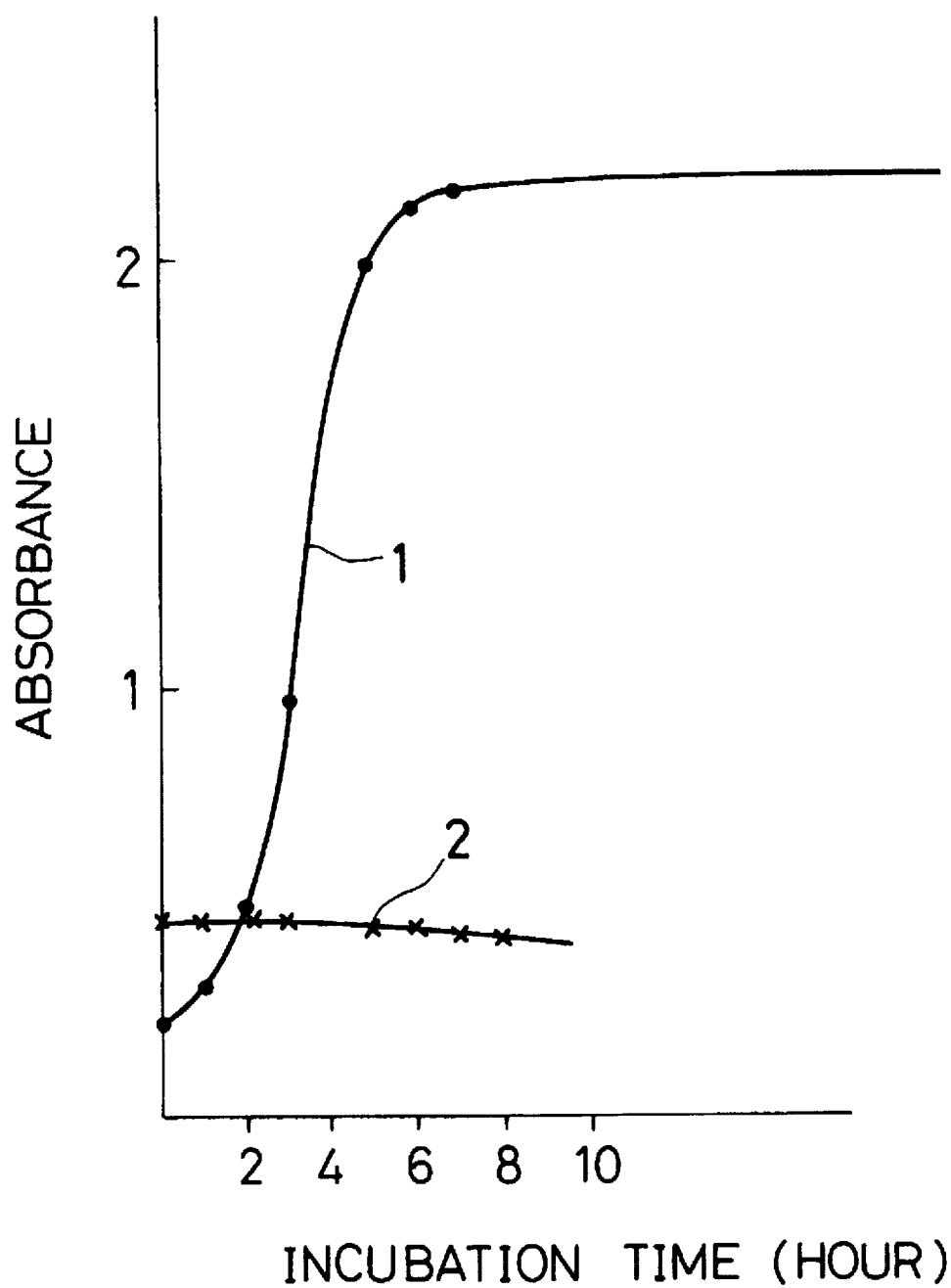
FIG. 1 is a diagram showing the results of tests of a culture medium for antibacterial activity obtained in Example 1 and Comparative Experiment 1.

The moiety —COR in the acyl glucosamine constituent unit of the partially N-acylated compound of a chitooligosaccharide of this invention is an acyl radical of 4 to 26 carbon atoms. If the number of carbon atoms of the acyl radical is 3 or less, the compound has little practical value. A compound which has 27 or more carbon atoms in the acyl radical is extremely difficult to synthesize. It is particularly appropriate from the practical point of view to adopt as the acyl radical mentioned above the product obtained by removing OH from an RCOOH selected from the group consisting of butyric acid, valeric acid, caproic acid, caprylic acid, captic acid, lauric acid, myristic acid, palmitic acid, stearic acid, linoleic acid, oleic acid, ricinoleic acid, lactic acid, sorbic acid, gluconic acid, phenylalanine, valine, leucine, methionine, and lysine.

As mentioned above, the partially N-acylated compound of chitooligosaccharide of this invention is composed of l number of acyl glucosamine constituent units, m number of glucosamine constituent units, and n number of acetyl glycosamine constituent units. The total of l+m+n is in the range of 3 to 20, preferably in the range of 3 to 9, and more preferably in the range of 6 to 9. Further, the numbers of the relevant constituent units l, m, and n are such that $l/l+m+n \times 100$, $m/l+m+n \times 100$ and $n/l+m+n \times 100$ which are respectively in the ranges of 5 to 80, 20 to 95, and 0 to 50, preferably in the ranges of 10 to 50, 50 to 90, and 0 to 10. These degrees of polymerization and the ratios of the respective contents are decided from the practical point of view.

The sequence in which the constituent units mentioned above are joined is not particularly restrictive except for the requirement that the terminal unit possess an —OH group at the 4 position or the 1 position thereof.

The partially N-acylated compound of chitooligosaccharide of this invention constituted as described above is useful as an antibacterial agent and as an additive to cosmetic products.

The antibacterial agent of this invention manifests antibacterial activity at a concentration in the approximate range of 0.05 to 0.5%. The microbes against which the antibacterial agent effective include such gram negative bacteria as coliform bacilli and salmonella bacteria and such gram positive bacteria as Staphylococcus, for example.

The cosmetic and personal care products to which the partially N-acylated compound of chitooligosaccharide of this invention is effectively added include emulsions, creams, deodorants, hair conditioners, shampoos, rinses, tooth pastes, bath lotions, and antibacterial sprays, for example. Further, the partially N-acylated compound of chitooligosaccharide of the invention is added to various substances such as detergents, starch pastes, tissue papers, disposable diapers and sanitary napkins. The compound is used as incorporated in or applied to such cosmetic, personal care products and other substances. The amount of the partially N-acylated compound of chitooligosaccharide of this invention to be applied to or incorporated in these products is not particularly restricted and may be appropriately decided by persons skilled in the art depending on the nature of the product. A guideline useful for determining the amount is shown below.

About 0.5% where antibacterial effect and moisture retaining effect are aimed at as in emulsions, creams, and deodorants;

About 0.1% where antibacterial effect is mainly aimed at as in shampoos, rinses, tooth pastes, and detergents; and About 0.1% in applications to tissue papers, disposable diapers, and sanitary napkins.

The partially N-acylated compound of chitooligosaccharide of this invention can be produced, for example, by hydrolyzing an alkali chitin solution thereby preparing chitosan, producing an acid solution of the chitosan, and hydrolyzing the resultant solution thereby forming a chitooligosaccharide, and acylating this chitooligosaccharide with an ordinary acylating agent (such as acid anhydride or acid chloride). As the material for the production, a chemically synthesized glucosamine oligomer may be used in the place of the chitooligosaccharide.

The chitin mentioned above is a polysaccharide which occurs in the shells of crabs, shrimps, and insects and in the cellular walls of such microbes as yeasts. The chitin from any of these sources can be used as the raw material for the production of the antibacterial agent of this invention. This chitin is deacetylated under an alkali condition to obtain chitosan. Since the deacetylation of chitin is difficult and expensive, it need not be implemented thoroughly. The chitosan is hydrolyzed with a mineral acid or an enzyme to obtain a chitooligosaccharide.

The chitooligosaccharide may be either a monosaccharide having a unique degree of polymerization or a mixture of chitooligosaccharides having diverse degrees of polymerization. Preferably, the mixture has the polymerization degree distribution thereof narrowed by the solvent fractionation technique. More appropriately, the mixture may be refined by any of various chromatographic techniques into an oligosaccharide having a fixed degree of polymerization.

The partially N-acylated compound of chitooligosaccharide of this invention can be produced by causing the chitooligosaccharide to react with an acylating agent such as, for example, acid anhydride or acid chloride in an ordinary solvent for saccharides such as, for example, water, alcohols represented by methanol or ethanol, or mixtures thereof under a neutral to acidic condition or in such a non-protonic organic solvent as dimethyl formamide, dimethyl acetamide, dimethyl sulfoxide, or pyridine under a neutral or basic condition.

The partially N-acylated compound of this invention manifests antibacterial activity when it contains the N-acyl radical at a fixed rate. For practical purposes, it tolerates partial inclusion therein of the O-acyl radical. So long as this compound contains the free amino group and the N-acyl radical at a ratio falling in the range mentioned above, this compound may include the O-acyl radical.

This invention is also directed to the salts of the partially N-acylated compound of chitooligosaccharide of this invention. The salts mentioned above are obtained by the reaction of the amino radical in the glucosamine of this compound with an acids. Concrete examples of the acid which forms a salt with the amino radical include such inorganic acids as hydrochloric acid, sulfuric acid, nitric acid, perchloric acid, hydrobromic acid, phosphoric acid, and boric acid and such organic acids as citric acid, acetic acid, propionic acid, maleic acid, fumaric acid, benzoic acid, p-toluene sulfonic acid, methane sulfonic acid, lactic acid, tartaric acid, succinic acid, saccharic acid, and gluconic acid.

The partially N-acylated compound of chitooligosaccharide of this invention is antibacterially active, soluble in water, highly water retentive. It also exhibits surface activity. Further, since it has an appropriate degree of biodegradability, it is gentle on living tissue and poses no problem of residual toxicity. It, therefore, is useful as an antibacterial agent and as an additive to cosmetic and personal care products.

In the salt of the partially N-acylated compound of chitooligosaccharide of this invention, the partially N-acylated compound of chitooligosaccharide moiety is substantially the active constituent. The uses found for this salt are nearly the same as those which are found for the partially N-acylated compound of chitooligosaccharide.

[EXAMPLES]

This invention will now be described more specifically below with reference to working examples.

In the following production examples, the number of amino radicals and the number (average) of N-acetyl radicals in the chitooligosaccharides as the raw material are fixed. In these production examples, the lauroyl radical is introduced into the amino radical (N-lauroylation). Since no substantial introduction of lauroyl radical into hydroxyl radical (O-lauroylation) occurs, the number of lauroyl radicals is determined by the conductometric titration technique.

The principle of the conductometric titration is represented by the following formula (A).

$$\text{Olig—NH}_2\cdot\text{HCl} + \text{NaOH} \rightarrow \text{Olig—NH}_2 + \text{NaCl} + \text{H}_2\text{O} \quad (A)$$

Figure 3:
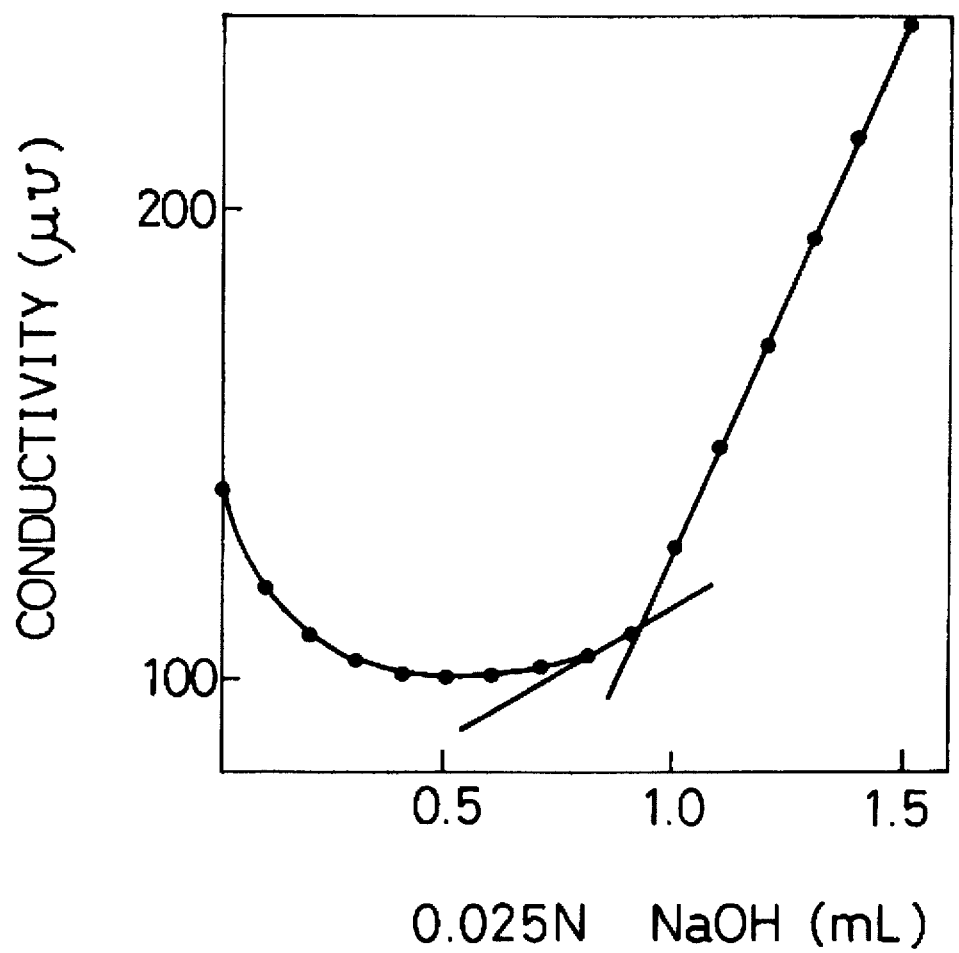
FIG. 3 is a graph showing the results of a conductometric titration performed on the partially N-acylated compound of a chitooligosaccharide of this invention having a ratio of lauroylation of 50% obtained in Production Example 2.

In the following working examples, 50 mL of the aqueous solution of hydrochloride of partially N-acylated oligosaccharide containing 10 to 20 mg of the hydrochloride of oligosaccharide was subjected to conductometric titration with the standard 0.025N NaOH solution. The equivalent point (0.931 mL) of the titration solution could be found because the conductivity rose suddenly when the amount of the standard NaOH solution used for the titration passed the equivalent point as shown in FIG. 3. As can be inferred from the formula (A) given above, the amino radical content could be determined because the NaOH equivalent weight used equals the equivalent weight of the amino radical in the sample.

Production Example 1

Two (2) g of the hydrochloride of chitooligosaccharide octamer (containing 1.1 N-acetyl radicals and 6.9 free amino radicals on the average per octamer) was dissolved in a mixed solution of 10% acetic acid (20 mL) and 1M sodium acetate (20 mL). Lauroyl chloride (0.44 mL) was dissolved in methanol (160 mL). The resultant solution was immediately mixed with the aforementioned solution of chitooligosaccharide octamer and the mixture was left reacting at normal room temperature for two hours. After the reaction, the reaction solution was acidified with hydrochloric acid and evaporated to dryness under a reduced pressure to expel the solvent by distillation. The solid precipitate consequently formed was extracted with ether and the by-product lauric acid was consequently removed. The remaining product was purified by the chromatographic technique (water as eluate) using a Sephadex G-25 Column to obtain an N-lauroyl oligosaccharide octamer partially introduced with N-lauroyl to have an average of 1.8 lauroyl radicals incorporated therein. By the conductometric titration for amino radical, the produced octamer was found to contain the glucosamine constituent units of the formulas (1) through (3) mentioned above at a formula (1):formula (2):formula (3) ratio of 1.8:5.1:1.1.

Production Example 2

An N-lauroyl oligosaccharide octamer (containing an average of 4 N-lauroyl groups per oligosaccharide) having a lauroylation ratio of 50% was obtained by following the procedure of Production Example 1 except for using the hydrochloride of an octamer of glucosamine of the formula (2) as the chitooligosaccharide octamer and using lauroyl chloride in an amount of 1.1 mL instead. The produced N-lauroyl oligosaccharide octamer was purified by the ion-exchange chromatographic technique using CM-Toyopearl 650S (CM-Toyopearl is a filler having an weakly acid ion-exchange capacity for chromatography, obtained by introducing a carboxymethyl radical to a gel filler medium having a hydrophilic vinyl polymer as a base material and is a product of Tosoh Corporation) as a filler. A 0.01N hydrochloric acid was used as the eluate and the elution curve was obtained by analyzing part of the eluate by the indole hydrochloric acid technique and determining the change in concentration of the aminosaccharide. The main elution section was fractionated by removing 10% portions each before and after the main peak. The produced lauroylated oligosaccharide octamer was found to possess four N-lauroyl groups by the conductometric titration technique.

By titration of 15.4 mg of the hydrochloride of the purified lauroylated oligosaccharide octamer with 0.025N NaOH, it was found to have an equivalent point at 0.931 mL of NaOH. The results indicate that the ratio of introduction of the lauroyl group was 50%. The results are shown in FIG. 3.

Production Example 3

An N-lauroyl oligosaccharide octamer (containing an average of 1.6 N-lauroyl groups per oligosaccharide octamer) having a lauroylation ratio of 20% was obtained by following the procedure of Production Example 1 except for using lauroyl chloride in an amount of 0.4 mL instead.

Examples 1 and 2 and Comparative Experiment 1

5-mL portions of an LB culture medium (prepared by combining 25.0 g of peptone, 12.5 g of yeast, 25.0 g of common salt, and 5.0 g of glucose, adjusting the resultant mixture to pH 7.2, and diluting the mixture to a total volume of 2.5 L with water) were added with the products of Production Examples 2 and 3 having N-lauroylation ratios of 20% and 50%, respectively, each at a concentration of 0.5%. The result was inoculated with a coliform bacilli solution (Examples 1 and 2). A sample was prepared at the same time by inoculating an LB culture medium containing no N-lauroylated chitooligosaccharide with the coliform bacilli solution (Comparative Experiment 1).

The three culture media were shaken at 37° C. to culture the bacteria. The growths of bacterial cells were determined by measuring the permeability at 600 nm with the aid of a spectrometer. The results are shown in FIG. 1 and FIG. 2.

Figure 2:
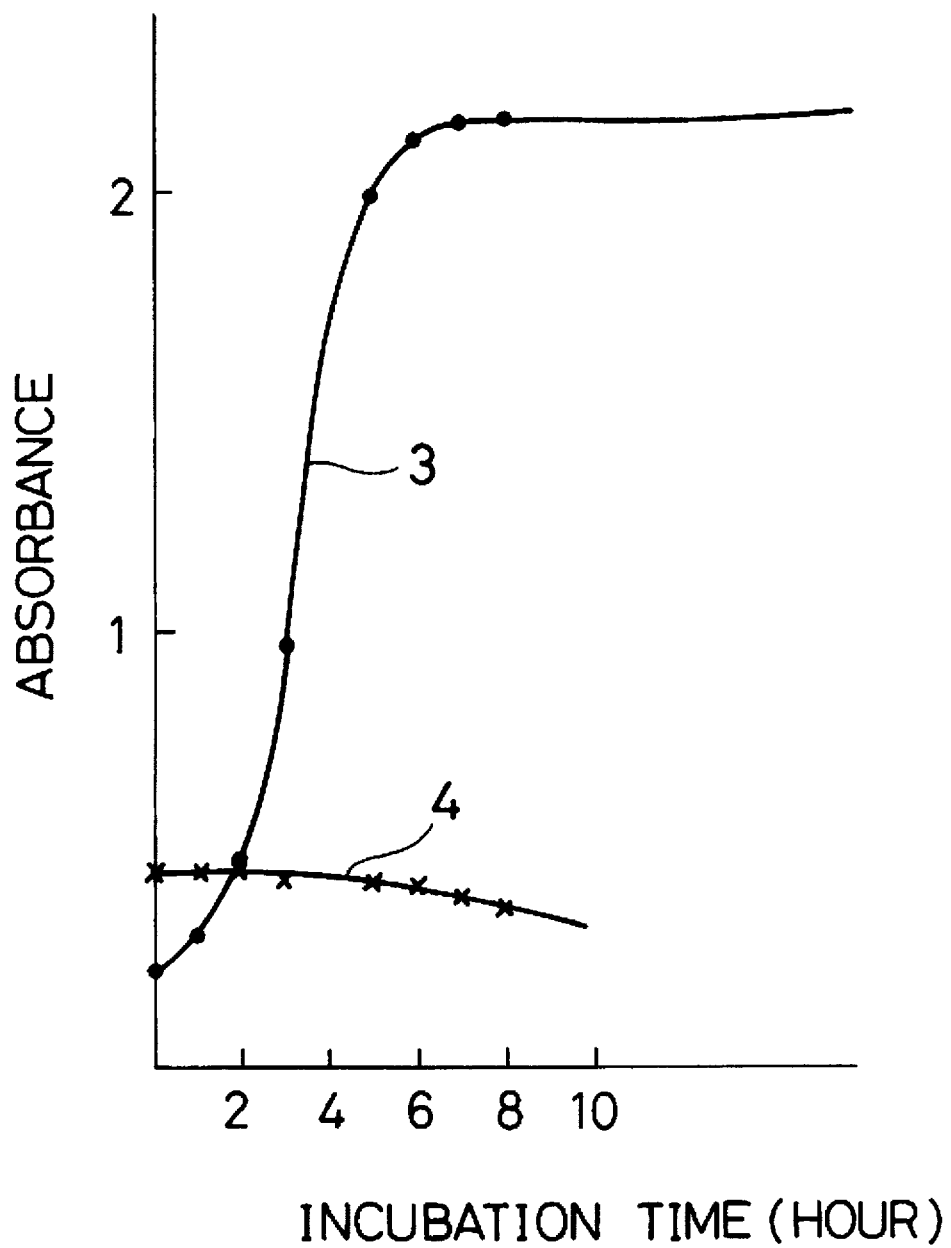
FIG. 2 is a diagram showing the results of tests of a culture medium for antibacterial activity obtained in Example 2 and Comparative Experiment 1.

In FIG. 1 and FIG. 2, the curves 1 and 3 represent the data obtained of the samples omitting the addition of chitooligosaccharide and the curves 2 and 4 represent the data obtained of the samples containing 0.5% of the partially N-acylated compounds of chitooligosaccharide of this invention having respective lauroylation ratios of 20% and 50%.

It can be seen from the results in FIG. 1 and FIG. 2 that the N-lauroylated chitooligosaccharide octamer completely prevented growth of coliform bacilli even under the optimum conditions (nutrition, temperature, and pH).

Example 3

A neutral cream containing the following components was manufactured by using the partially N-lauroyl chitooligosaccharide octamer obtained in Production Example 1. The components were highly compatible. The produced cream exhibited excellent anti-bacterial power, moisture retaining effect and quality.

| Component | Amount used (%) |
|---|---|
| Purified water | 50.3 |
| Glycerin | 5.0 |
| Dipropylene glycol | 5.0 |
| Sodium pyrrolidone carbonate | 1.0 |
| 1,3-Butylene glycol | 3.0 |
| Polyoxyethylene glyceryl monostearate | 1.2 |
| Glycerin monostearate | 1.3 |
| Potassium stearate | 2.0 |
| Cetostearyl alcohol | 2.5 |
| Reducing lanolin | 3.0 |
| Shortening oil | 5.0 |
| Vaseline | 5.0 |
| Squalane | 10.0 |

-continued

| Component | Amount used (%) |
| --- | --- |
| Cetyl-2-ethylhexanoate | 5.0 |
| Perfume | 0.2 |
| N-lauroyl chitooligosaccharide octamer | 0.5 |

Production Example 4

Two (2) g of hydrochloride powder of the heptamer of glucosamine of the formula (2) containing no acetyl group was dispersed in 30 ml of dimethylformamide (DMF). The resultant dispersion was added with 1 ml of triethyl amine. A solution of 0.7 g of stearoyl chloride in 30 ml of DMF was added dropwise to the resultant dispersion under stirring over a period of about 30 minutes. The result was continuously stirred at normal room temperature for two hours to complete the reaction. The reaction solution was evaporated to dryness under reduced pressure. The residue was dispersed in 100 ml of water, acidified with hydrochloric acid, and extracted with ether to remove stearic acid. The insoluble component dispersed in the water phase was separated by filtration, washed with water, and dried. Meanwhile, the filtrate was neutralized with sodium hydroxide and purified by chromatography (water as eluate) with a Sephadex G25 Column. The produced oligosaccharide was found to have acquired an average of 2.2 stearoyl groups. The introduced amount was confirmed by the conductometric titration of amino radical. The water-insoluble section, based on the results of infrared absorption spectral analysis, was identified to be a section having a large introduced N-stearoyl group content and partially containing an O-stearoylated compound.

What is claimed is:

1. A partially N-acylated compound of a chitooligosaccharide consisting essentially of a) l number of acyl glucosamine constituent units represented by the formula;

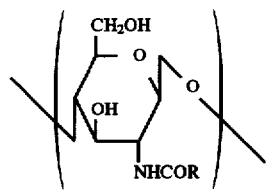

wherein —COR stands for an acyl radical of 4 to 26 carbon atoms, b) m number of glucosamine constituent units represented by the formula:

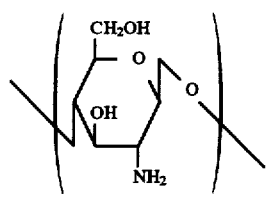

and c) n number of acetyl glucosamine constituent units represented by the formula:

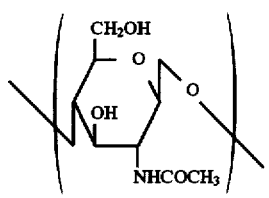

wherein l, m, and n satisfy the following equations, $l/(l+m+n) \times 100 = 5 \sim 80$, $m/(l+m+n) \times 100 = 20 \sim 95$, $n/(l+m+n) \times 100 = 0 \sim 50$, $l+m+n = 3 \sim 20$, and possessing an OH group at the 4 position or 1 position of the terminal constituent unit.

2. The compound according to claim 1, wherein the total of l+m+n is in the range of 3 to 9.

3. The compound according to claim 1, wherein the total of l+m+n is in the range of 6 to 9.

4. The compound according to claim 1, wherein the acyl radical in said acyl glucosamine constituent unit is a product obtained by removing OH from an RCOOH selected from the group consisting of butyric acid, valeric acid, caproic acid, caprylic acid, capric acid, lauric acid, myristic acid, palmitic acid, stearic acid, linoleic acid, oleic acid, ricinoleic acid, lactic acid, sorbic acid, gluconic acid, phenylalanine, valine, leucine, methionine, and lysine.

5. An antibacterial agent comprising a partially N-acylated compound of chitooligosaccharide as set forth in claim 1 and a suitable carrier.

6. The antibacterial agent according to claim 5, wherein the total of l+m+n is 9 and the acyl radical in said acyl glucosamine constituent unit is the product obtained by removing OH from an RCOOH selected from the group consisting of butyric acid, valetic acid, caproic acid, caprylic acid, captic acid, lauric acid, myristic acid, palmitic acid, stearic acid, linoleic acid, oleic acid, ricinoleic acid, lactic acid, sorbic acid, gluconic acid, phenylalanine, valine, leucine, methionine, and lysine.

7. The antibacterial agent according to claim 5, wherein said partially N-acylated compound is contained in a concentration of about 0.05 to 0.5%.

8. An additive for a personal care product comprising a partially N-acylated compound of chitooligosaccharide a set forth in claim 1.

9. The compound according to claim 1, wherein $l/(l+m+n) \times 100 = 10 \sim 50$.

10. The compound according to claim 1, wherein $m/(l+m+n) \times 100 = 50 \sim 90$.

11. The compound according to claim 1, wherein $n/(l+m+n) \times 100 = 0 \sim 10$.

12. A salt of a partially N-acylated compound of a chitooligosaccharide obtained by reacting with an acid an amino radical in the glucosamine of a partially N-acylated compound of a chitooligosaccharide consisting essentially of a) l number of acyl glucosamine constituent units represented by the formula;

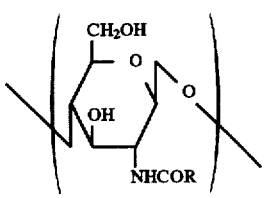

(1)

wherein —COR stands for an acyl radical of 4 to 26 carbon atoms, b) m number of glucosamine constituent units represented by the formula:

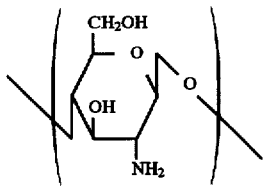

(2)

and c) n number of acetyl glucosamine constituent units represented by the formula:

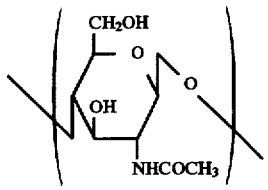

(3)

whereby l, m, and n satisfy the following equations, $l/(l+m+n) \times 100 = 5\text{–}80$, $m/(l+m+n) \times 100 = 20\text{–}95$, $n/(l+m+n) \times 100 = 0\text{–}50$, $l+m+n = 3\text{–}20$, and possessing an OH radical at the 4 position or 1 position of the terminal constituent unit.

13. The salt according to claim 12, wherein said acid is one member selected from the group consisting of hydrobromic acid, sulfuric acid, nitric acid, perchloric acid, hydrobromic acid, phosphoric acid, boric acid, citric acid, acetic acid, propionic acid, maleic acid, fumaric acid, benzoic acid, p-toluene sulfonic acid, methane sulfonic acid, lactic acid, tartaric acid, succinic acid, saccharic acid, and gluconic acid.

14. The salt according to claim 12, wherein the total of l+m+n is in the range of 3 to 9.

15. The salt according to claim 12, wherein the total of l+m+n is in the range of 6 to 9.

16. The salt according to claim 12, wherein the acyl radical in said acyl glucosamine constituent unit is a product obtained by removing OH from an RCOOH selected from the group consisting of butyric acid, valeric acid, caproic acid, caprylic acid, capric acid, lauric acid, myristic acid, palmitic acid, stearic acid, linoleic acid, oleic acid, ricinoleic acid, lactic acid, sorbic acid, gluconic acid, phenylalanine, valine, leucine, methionine, and lysine.

17. The salt according to claim 12, wherein $l/(l+m+n) \times 100 = 10\text{–}50$.

18. The salt according to claim 12, wherein $m/(l+m+n) \times 100 = 50\text{–}90$.

19. The salt according to claim 12, wherein $n/(l+m+n) \times 100 = 0\text{–}10$.

* * * * *